US012721634B2

(12) United States Patent
Zehavi et al.

(10) Patent No.: US 12,721,634 B2
(45) Date of Patent: Sep. 1, 2026

(54) DRILLING TOOL, SYSTEMS, AND METHODS

(71) Applicant: Mazor Robotics Ltd., Caesarea (IL)

(72) Inventors: Eli Zehavi, Tel Aviv (IL); Arik Levy, Herzliya (IL)

(73) Assignee: Mazor Robotics Ltd., Caesarea (IL)

( * ) Notice: Subject to any disclaimer, the term of this patent is extended or adjusted under 35 U.S.C. 154(b) by 2 days.

(21) Appl. No.: 18/792,133

(22) Filed: Aug. 1, 2024

(65) Prior Publication Data

US 2024/0390015 A1 Nov. 28, 2024

Related U.S. Application Data

(62) Division of application No. 17/339,708, filed on Jun. 4, 2021, now Pat. No. 12,076,027.

(60) Provisional application No. 63/039,818, filed on Jun. 16, 2020.

(51) Int. Cl.

| | |
|---|---|
| ***A61B 17/16*** | (2006.01) |
| ***A61B 17/3209*** | (2006.01) |
| ***A61B 34/30*** | (2016.01) |
| ***A61M 29/00*** | (2006.01) |

(52) U.S. Cl.
CPC ...... *A61B 17/1615* (2013.01); *A61B 17/1637* (2013.01); *A61B 17/32093* (2013.01); *A61B 34/30* (2016.02); *A61M 29/00* (2013.01)

(58) Field of Classification Search
CPC .. A61B 17/02–17/0293; A61B 17/16–17/1697
See application file for complete search history.

(56) References Cited

U.S. PATENT DOCUMENTS 4,386,602 A * 6/1983 Sheldon ................ A61M 29/02 600/102
7,749,225 B2 7/2010 Chappuis et al.
9,216,015 B2 * 12/2015 Wilson ............... A61B 17/3431
(Continued)

FOREIGN PATENT DOCUMENTS

CN 102846353 1/2013
CN 103547227 1/2014
(Continued)

OTHER PUBLICATIONS

International Search Report and Written Opinion for International (PCT) Patent Application No. PCT/IB2021/055333, dated Sep. 14, 2021 14 pages.
(Continued)

*Primary Examiner* — Zade Coley
(74) *Attorney, Agent, or Firm* — Sheridan Ross PC

(57) ABSTRACT

A surgical tool comprises a dilator, a cutter, a retractable brush, and at least one retractable drill. The dilator is configured to dilate tissue of a patient and can be positioned in an undilated configuration or a dilated configuration. The cutter is configured to cut the tissue and is disposed at a distal end of the dilator. The cutter is configured to move between a cutting position when the dilator is in the undilated configuration and a non-cutting position when the dilator is in the dilated configuration. The retractable brush is configured to brush a surface of an anatomical element of the patient to remove matter from the surface. The at least one retractable drill is configured to drill into the anatomical element.

10 Claims, 5 Drawing Sheets

(56) References Cited

U.S. PATENT DOCUMENTS

| | | | | |
|---|---|---|---|---|
| 10,292,726 | B2 | 5/2019 | O'Neil et al. | |
| 10,485,528 | B2 | 11/2019 | Sweeney | |
| 12,076,027 | B2 | 9/2024 | Zehavi et al. | |
| 2006/0142775 | A1 * | 6/2006 | Heneberry ....... | A61B 17/32002 606/80 |
| 2007/0185513 | A1 | 8/2007 | Woolfson et al. | |
| 2010/0100032 | A1 * | 4/2010 | Hassidov ........... | A61B 17/3439 604/99.04 |
| 2011/0152866 | A1 * | 6/2011 | Knutson ............ | A61B 17/3472 606/86 R |
| 2011/0251616 | A1 | 10/2011 | Osman et al. | |
| 2017/0224358 | A1 * | 8/2017 | Kostrzewski .......... | A61B 34/30 |
| 2017/0281145 | A1 | 10/2017 | Crawford et al. | |
| 2018/0036114 | A1 | 2/2018 | Pilgeram et al. | |
| 2018/0070936 | A1 | 3/2018 | Miles et al. | |
| 2018/0200016 | A1 | 7/2018 | Chappuis et al. | |
| 2020/0054350 | A1 | 2/2020 | Miller | |
| 2021/0100567 | A1 * | 4/2021 | Sharifi-Mehr ..... | A61B 17/3496 |

FOREIGN PATENT DOCUMENTS

| | | |
|---|---|---|
| CN | 105636635 | 6/2016 |
| CN | 104815388 | 10/2017 |
| CN | 109688963 | 4/2019 |
| EP | 1553882 | 7/2005 |
| EP | 2526882 | 11/2012 |
| KR | 10-2006-0094733 | 8/2006 |
| WO | WO 2018/144988 | 8/2018 |

OTHER PUBLICATIONS

International Preliminary Report on Patentability for International (PCT) Patent Application No. PCT/IB2021/055333, dated Dec. 29, 2022 9 pages.

Official Action for U.S. Appl. No. 17/339,708, dated Oct. 3, 2023 9 pages Restriction Requirement.

Official Action for U.S. Appl. No. 17/339,708, dated Jan. 9, 2024 8 pages.

Notice of Allowance for U.S. Appl. No. 17/339,708, dated Apr. 30, 2024 5 pages.

Official Action with English Translation for China Patent Application No. 202180036889.7, dated Jan. 22, 2026, 19 pages.

* cited by examiner

DRILLING TOOL, SYSTEMS, AND METHODS

CROSS REFERENCE TO RELATED APPLICATIONS

This application is a division of U.S. application Ser. No. 17/339,708, filed on Jun. 4, 2021, which claims the benefit of U.S. Provisional Application No. 63/039,818, filed on Jun. 16, 2020, the disclosures of which applications are incorporated herein by reference in their entireties.

FIELD

The present technology is generally related to surgical tools, and is more specifically related to tools for surface preparation and drilling.

BACKGROUND

During a surgical procedure, and in particular during a bone drilling procedure, multiple surgical tools may be used to prepare a surface of an anatomical element for drilling and to drill into the anatomical element. Skiving, or a drill's inability to engage with the anatomical element such that the drill slides on the surface of the anatomical element, sometimes occurs during drilling.

SUMMARY

Example aspects of the present disclosure include:

A tool according to at least one embodiment of the present disclosure comprises a dilator configured to dilate tissue of a patient, the dilator having a plurality of arms with each arm having a distal end, the dilator having an undilated configuration and a dilated configuration, the distal ends of the plurality of arms being located closer to each other when the dilator is in the undilated configuration than when the dilator is in the dilated configuration; a cutter configured to cut the tissue, the cutter disposed at the distal end of one of the plurality of arms and configured to move between a cutting position when the dilator is in the undilated configuration and a non-cutting position when the dilator is in the dilated configuration; a retractable brush configured to brush a surface of an anatomical element of the patient to remove matter from the surface; and at least one retractable drill configured to drill into the anatomical element.

Any of the aspects herein, wherein the dilator may be biased to the undilated configuration.

Any of the aspects herein, wherein extending the brush from a retracted position to an extended position may move the dilator from the undilated position to the dilated position.

Any of the aspects herein, wherein the cutter may move from the cutting position to the non-cutting position as the dilator moves from the undilated configuration to the dilated configuration.

Any of the aspects herein, wherein the brush may be automatically retracted when the at least one retractable drill is extended.

Any of the aspects herein, wherein the at least one retractable drill may comprise a first drill and a second drill, the second drill being disposed in a cannula of the first drill.

Any of the aspects herein, wherein the brush and the first drill may be automatically retracted when the second drill is in operation.

Any of the aspects herein, wherein the second drill may be extendable and retractable separately from the first drill.

Any of the aspects herein, wherein the first drill may be a burr configured to create a flat or dimple on the surface of the anatomical element and the second drill is a drill bit configured to drill a hole through the flat or dimple.

Any of the aspects herein, wherein the tool may further comprise a first casing and a second casing disposed inside of the first casing.

Any of the aspects herein, wherein each of the plurality of arms may be rotatably connected to the first casing.

Any of the aspects herein, wherein the brush may extend from an end of the second casing, and the second casing is rotatable within the first casing.

Any of the aspects herein, wherein the at least one retractable drill may be disposed inside of the second casing when retracted.

Any of the aspects herein, wherein each of the first casing and the second casing may be a tube.

Any of the aspects herein, wherein the cutter may be selectively rotatable from the cutting position to the non-cutting position.

Any of the aspects herein, wherein the cutter may be configured to rotate from the cutting position to the non-cutting position upon engagement with the tissue during movement of the dilator from the undilated configuration to the dilated configuration.

A method for drilling into an anatomical element according to one embodiment of the present disclosure comprises cutting tissue of a patient using a cutter of a surgical tool; dilating the tissue of the patient using a dilator of the surgical tool, the dilator having a plurality of arms, each arm having a free end, the plurality of arms moveable between an undilated position, in which the free ends are closer to each other to define a wedge-like configuration, and a dilated position in which the free ends are further from each other than in the undilated position; cleaning a surface of an anatomical element of the patient to remove matter from the surface using a brush of the surgical tool; and drilling into the anatomical element with at least one drill of the surgical tool.

Any of the aspects herein, wherein the method may be performed automatically by a robotic arm holding the surgical tool.

Any of the aspects herein, wherein the method may further comprise cutting a flat into the surface of the anatomical element using the at least one drill.

Any of the aspects herein, wherein dilating the tissue may include extending the brush adjacent the dilator to move the plurality of arms from the undilated position to the dilated position.

A system for minimally invasive drilling according to one embodiment of the present disclosure comprises a processor; and a memory storing instructions for execution by the processor that, when executed, cause the processor to: cause a cutter of a surgical tool to cut tissue of a patient, cause a dilator of the surgical tool to dilate the tissue, cause a brush of the surgical tool to brush a surface of an anatomical element of the patient to remove matter from the surface, and cause a drill of the at least one surgical tool to drill the anatomical element.

Any of the aspects herein, wherein the system may further comprise at least one robotic arm, wherein the surgical tool is disposed on an end of the at least one robotic arm.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1B:
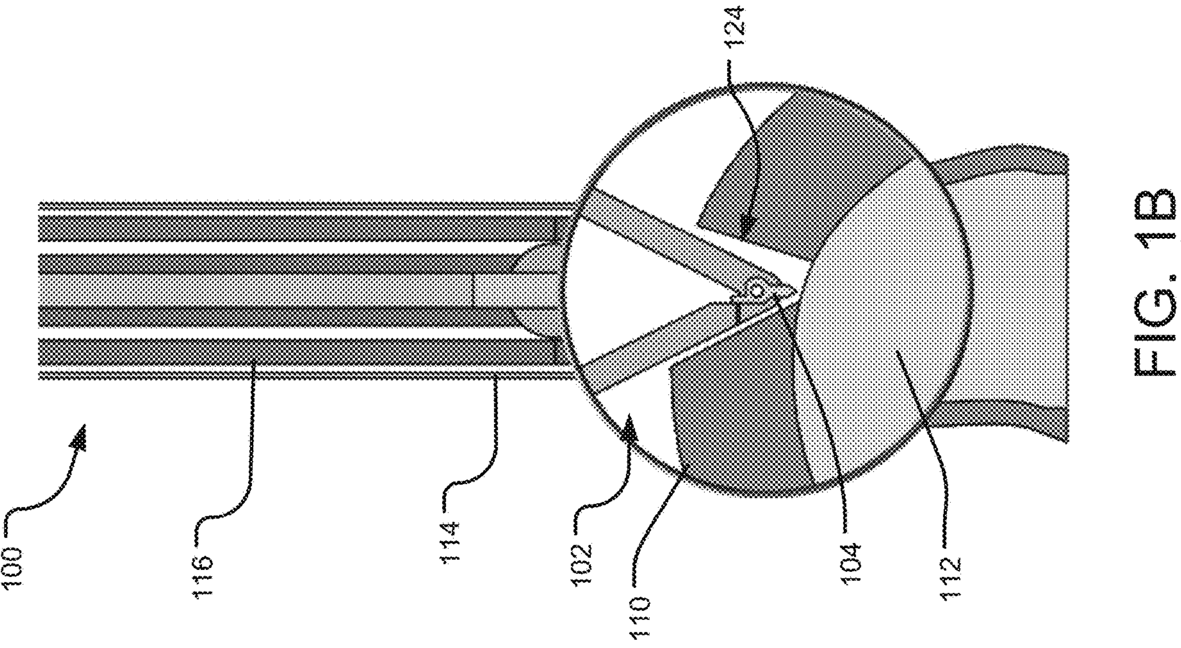
FIG. 1B depicts a close-up view of the drilling tool of FIG. 1A according to at least another embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the methods of this disclosure may be performed by a combination of units or modules associated with, for example, a computing device and/or a medical device (including a medical imaging device).

In one or more examples, one or more steps of the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure. Also, unless explicitly stated otherwise, terms such as "about" and "approximately" when used in connection with a stated value mean within ten percent of the stated value.

One of the challenges of drilling into bone is skiving. Skiving occurs due to the angle at which the drill bit impacts the bone and/or the presence of soft tissue on the bone. The present disclosure describes devices, systems, and methods for reducing or avoiding skiving. Embodiments of the present disclosure utilize a robotic end effector on a robotic arm. The robotic end effector holds a single tool controllable by the root to make a skin incision, dilate the incision, prepare the surface of an anatomical element for drilling, and drill into the anatomical element. The use of a robotic arm enables control of the position and orientation of the tool (including, for example, a height of the tool above a patient's skin and/or above the target anatomical element, as well as the direction in which the tool is oriented.

A drilling tool as described herein comprises a penetration dilator, a metal brush, a burr, and a drill bit. The penetration dilator is used to simultaneously cut through and dilate the soft tissue above the target anatomical element. The penetration dilator comprises a special plate that is active during penetration of the soft tissue and inactive when the penetration dilator moves to a dilated position. Once the penetration dilator is fully dilated, a surface of the anatomical element is then cleaned with the metal brush, after which the burr is used to cut a flat or dimple in the surface of the anatomical element. The flat or dimple acts to guide the drill bit to the right trajectory in order to eliminate skiving. The drill bit may then be used to drill into or to mill the anatomical element.

Embodiments of the present disclosure may be particularly useful, for example, during minimally invasive surgery, including minimally invasive spine surgery.

Inclusion of a cutting blade, dilator, brush, burr, and drill in a single tool significantly reduces the number of tool changes needed for drilling in a minimally invasive procedure, while reducing the likelihood of skiving and thus increasing the effectiveness and accuracy of the procedure.

In some applications, multiple tools may be used to gain access to and then adequately clean a surface of an anatomical element, and/or to mill or otherwise prepare a surface of the anatomical element for drilling. However, the use of multiple tools may be cumbersome and time consuming. Further, the multiple tools may not adequately prepare the surface and thus may not adequately reduce the likelihood of skiving during drilling.

Embodiments of the present disclosure provide a single, multi-function tool that can prepare an anatomical element for drilling without any need to switch tools, thereby decreasing overall operating complexity, time, and cost. Tools according to embodiments of the present disclosure are also advantageously small and non-intrusive, and may be suitable for minimally invasive procedures. Embodiments of the present disclosure also provide for tools that can prepare the anatomical element to prevent or reduce a skiving effect.

As described more fully below, a drilling tool according to at least some embodiments of the present disclosure may be designed to form and dilate an opening in a tissue of a patient, prepare a surface of an anatomical element exposed by the opening for drilling, and drilling the anatomical element, all using components disposed or formed in a single housing of a single tool.

Figure 1A:
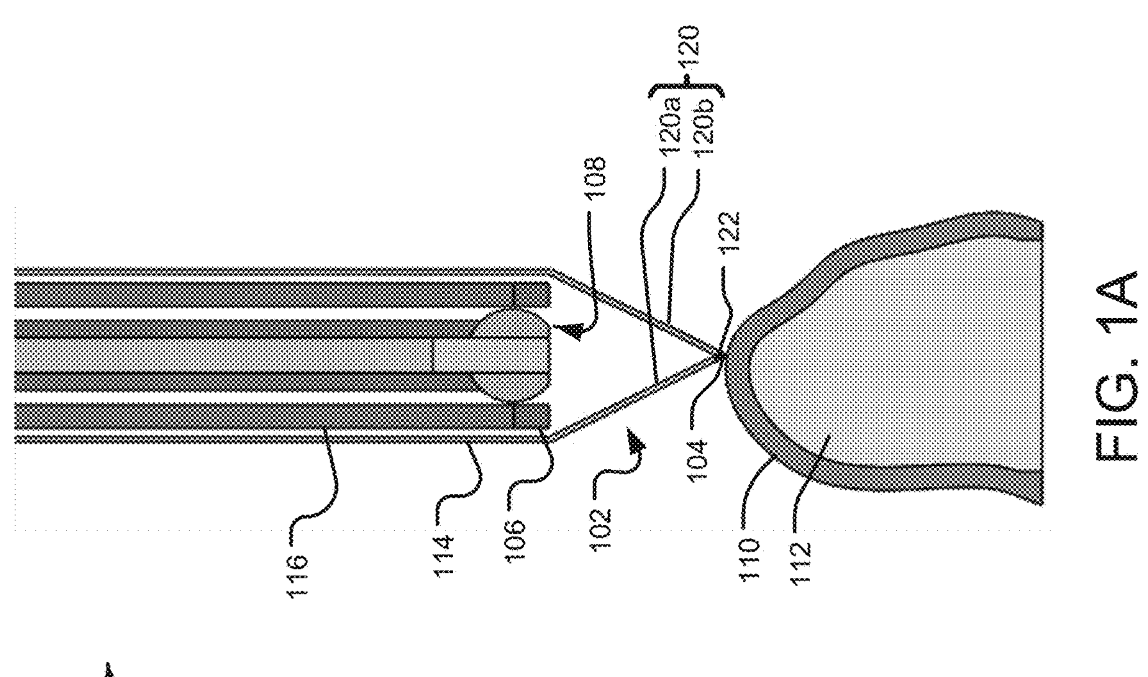
FIG. 1A depicts a drilling tool according to at least one embodiment of the present disclosure.

With reference first to FIGS. 1A and 1B, a drilling tool 100 according to at least one embodiment of the present disclosure comprises a dilator 102, a cutter 104, a retractable brush 106, and at least one retractable drill 108. In some embodiments, the tool 100 may have fewer components or more components. The drilling tool 100 may be used to cut and dilate tissue 110 of a patient, remove soft tissue from a surface of an anatomical element 112 (which may be, for example, a bone), cut a flat or dimple into the surface, and drill into the anatomical element 112 using a single tool 100 to perform each step during a surgical procedure. The tool 100 may be held by a robot 404, as described with respect to FIG. 4, and may automatically (e.g., under control of the robot 404) or manually (e.g., under control of a surgeon) perform each step.

In the illustrated embodiment, the tool 100 includes a first casing 114 and a second casing 116 housed inside of the first casing 114. In other embodiments, the tool 100 may have one casing or more than two casings. Each of the first casing 114 and the second casing 116 is tubular or cylindrical, though in other embodiments the casings 114, 116 may be any shape including, but not limited to, square, rectangular, triangular, oval, or the like. Each casing 114, 116 may be formed of the same material, or each casing 114, 116 may be formed of a different material from each other. The material may be any solid material including, but not limited to, metal, steel, plastic, or the like, or any combination thereof, and may be biocompatible. In the illustrated embodiment, the at least one retractable drill 108 is partially or fully disposed inside a bore of the second casing 116, the retractable brush 106 is disposed inside the first casing 114 and at an end of the second casing 116, and the dilator 102 and the cutter 104 are disposed at an end of the first casing 114. In other embodiments, the at least one retractable drill 108 may be disposed inside the first casing 114 (e.g., between the first casing 114 and the second casing 116), the retractable brush 106 may be disposed inside the second casing 116, and/or the dilator 102 and the cutter 104 may be disposed at an end of the second casing 116.

As shown in FIG. 1B, the cutter 104 (which may also be referred to herein as a blade or a cutting blade) is configured to cut through soft tissue 110 to form an incision having an opening 124 during initial insertion of the tool 100, when the dilator 102 is in an undilated position (also referred to herein as an undilated configuration), described in more detail below. The cutter 104 may be replaceable or repairable when the cutter 104 becomes dull. During use, the tool 100 may be extended until the cutter 104 contacts an anatomical element 112 beneath the tissue 110. In the illustrated example, the cutter 104 is disposed at a free end or distal end 122 of one of a plurality of arms 120. Described in more detail with respect to FIGS. 2A and 2B below, the plurality of arms 120 may comprise arms 120*a*, 120*b*. In other examples, the tool 100 can have more than one cutter 104. For example, a cutter 104 may be disposed at the free end or distal end 122 of each of the plurality of arms 120 or of more than one arm of the plurality of arms 120. The cutter 104 is positioned in a cutting position when the dilator 102 is in the undilated position or configuration, shown in FIG. 1B, and in a non-cutting position, shown in FIG. 2B, when the dilator 102 is in a dilated position or configuration, described in more detail below. In some embodiments, the cutter 104 is selectively rotatable from the cutting position to the non-cutting position, as visible in FIG. 2B. The cutter 104 may be configured to automatically rotate from the cutting position to the non-cutting position when the dilator 102 transitions from the undilated position to the dilated position. Also in some embodiments, the cutter 104 may be configured to automatically rotate from the non-cutting position to the cutting position when the cutter 104 engages the tissue 110 during movement of the dilator 102 from the undilated position or configuration to the dilated position or configuration. Stated differently, movement of the dilator 102 from the undilated configuration to the dilated configuration causes the cutter 104 to move from the cutting position to the non-cutting position. In other examples, the cutter 104 may be retracted or removed when in the non-cutting position.

In some embodiments, the cutter 104 is biased to the cutting position, though in other embodiments, the cutter 104 is biased to the non-cutting position or is not biased to either position. The cutter 104 may be held or locked in the non-cutting position or the cutting position. The non-cutting position advantageously relieves pressure on and/or undesired cutting of the tissue 110 when the dilator 102 is in the dilated position. In other words, if the cutter 104 remains in the cutting position when the dilator 102 is in the dilated position, the tissue 110 proximate the free end 122 of arm 120*b* may experience additional, unnecessary cuts, thereby damaging the tissue. Similarly, the rotatability of the cutter 104 enables the cutter 104 to move to the non-cutting position when dilation begins, so as to rotate or fold the cutter 104 without further cutting the tissue 110 during dilation.

Figure 2B:
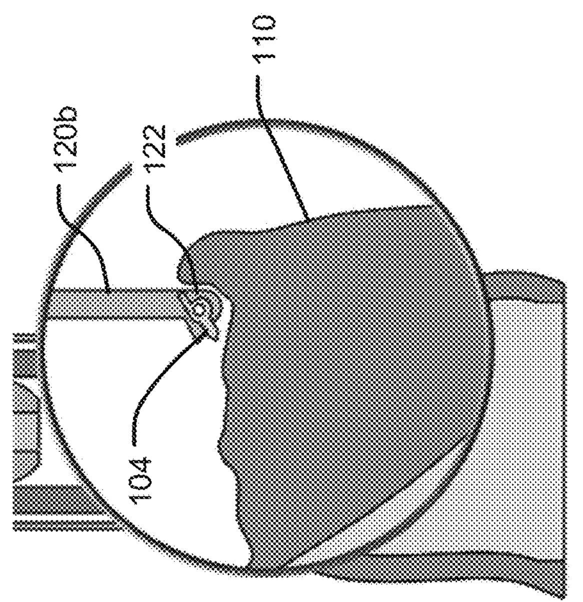
FIG. 2B depicts a close-up view of FIG. 2A according to at least another embodiment of the present disclosure.
Figure 2A:
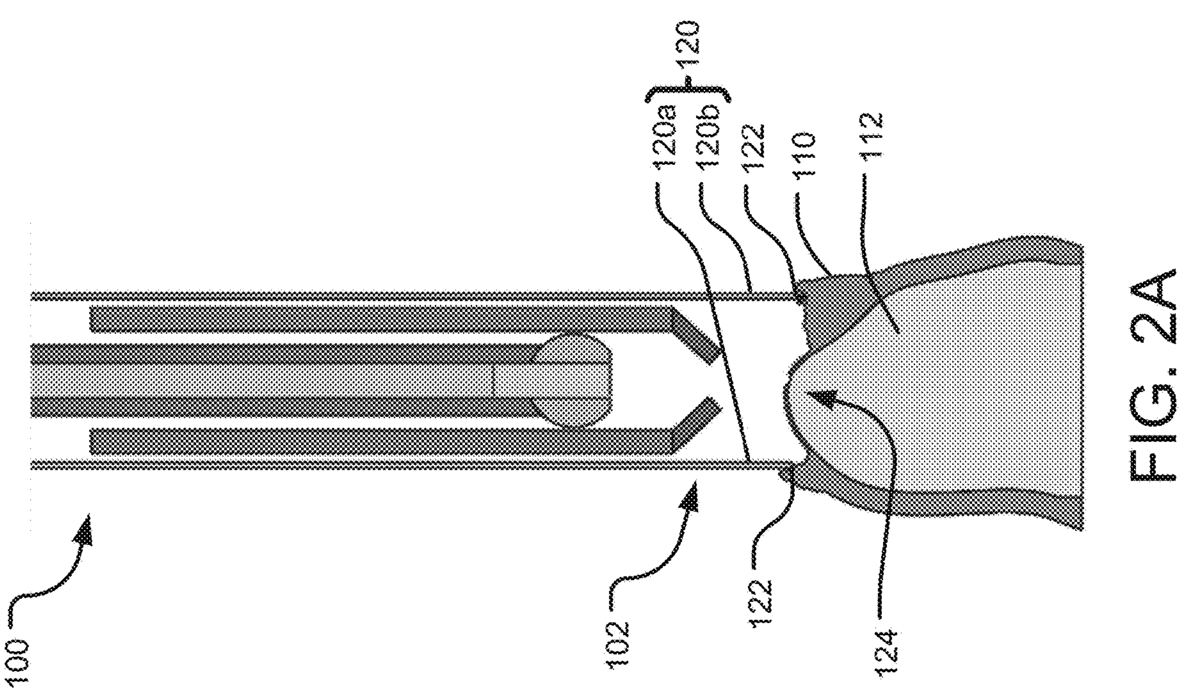
FIG. 2A depicts the drilling tool of FIG. 1 according to at least another embodiment of the present disclosure.

Turning to FIGS. 2A and 2B, use of the dilator 102 is shown. The dilator 102 is configured to dilate the tissue 110 of a patient and includes the plurality of arms 120. In the illustrated example, the plurality of arms 120 comprises the two arms 120*a*, 120*b*, though in other embodiments, the plurality of arms 120 may comprise more than two arms. Each arm 120*a*, 120*b* includes the free end 122. The plurality of arms 120 is rotatably connected to the end of the first casing 114, and each arm 120*a*, 120*b* is operable to rotate from the undilated position, shown in FIG. 1A, to the dilated position, shown in FIG. 2A. In the illustrated embodiment, the free or distal ends 122 meet to define a point when the plurality of arms 120 is in the undilated position or configuration, and the free or distal ends 122 are separated from each other when the plurality of arms 120 is in the dilated position or configuration. In other embodiments, the free or distal ends 122 may be located closer to each other, but not in contact, when the dilator 102 is in the undilated position or configuration.

In the illustrated embodiment, each arm 120*a*, 120*b* is positioned opposite the other, though in other embodiments, each arm 120*a*, 120*b* may be positioned anywhere on a perimeter of the end of the first casing 114. Each arm 120*a*, 120*b* angles inward and contacts the other arm 120*b*, 120*a*, respectively, to form a wedge or triangle when the plurality of arms 120 is in the undilated position. In embodiments where the plurality of arms 120 comprise more than two arms, each arm may meet at the point to form a partial or a full conc.

In some embodiments, the plurality of arms 120 is biased (e.g., by a spring) to the undilated position (e.g., the insertion position), and thus, remains in the undilated position until actuated or otherwise forced to rotate to the dilated position. In other embodiments, the plurality of arms 120 may be biased to the dilated position and held in the undilated position (e.g., during insertion) by a force. When the force acting on the plurality of arms 120 is removed or withdrawn, the plurality of arms 120 moves into the dilated position. In other embodiments, the plurality of arms 120 may not be biased to either position.

In some embodiments, the plurality of arms 120 is actuated by extending the retractable brush 106, which pushes against and applies a force to the plurality of arms 120, to rotate the plurality of arms 120 from the undilated position to the dilated position. The plurality of arms 120 may lock into the dilated position such that the plurality of arms 120 remains in the dilated position when the retractable brush 106 is retracted back into the first casing 114 and the force is removed from the plurality of arms 120. In some embodiments, the plurality of arms 120 may rotate back to the undilated position when the retractable brush 106 is retracted and releases the force on the plurality of arms 120. In other embodiments, the plurality of arms 120 may be actuated by a controller (not shown), the robot 404, and/or a surgeon. As illustrated, when the plurality of arms 120 is in the dilated position, each arm of the plurality of arms 120 is parallel to or in line with the first casing 114. In other embodiments, however, each arm of the plurality of arms 120 may not be parallel to or in line with the first casing 114 when in the dilated position. For example, rotation of each arm of the plurality of arms may from the undilated position to the dilated position may cease when the plurality of arms is not yet parallel to or in line with the first casing 114 (e.g., the plurality of arms may be angled toward a central axis of the first casing 114), or when the plurality of arms is past parallel to or in line with the first casing 114 (e.g., the plurality of arms may be angled away from a central axis of the first casing 114). An amount of rotation of the plurality of arms 120 may correspond to an amount of dilation of the tissue 110. In other words, a spacing between the free ends 122 of the plurality of arms 120 when in the dilated position may correspond to a maximum width or diameter of the opening 124 of the tissue 110.

Figures 3A, 3B, 3C:
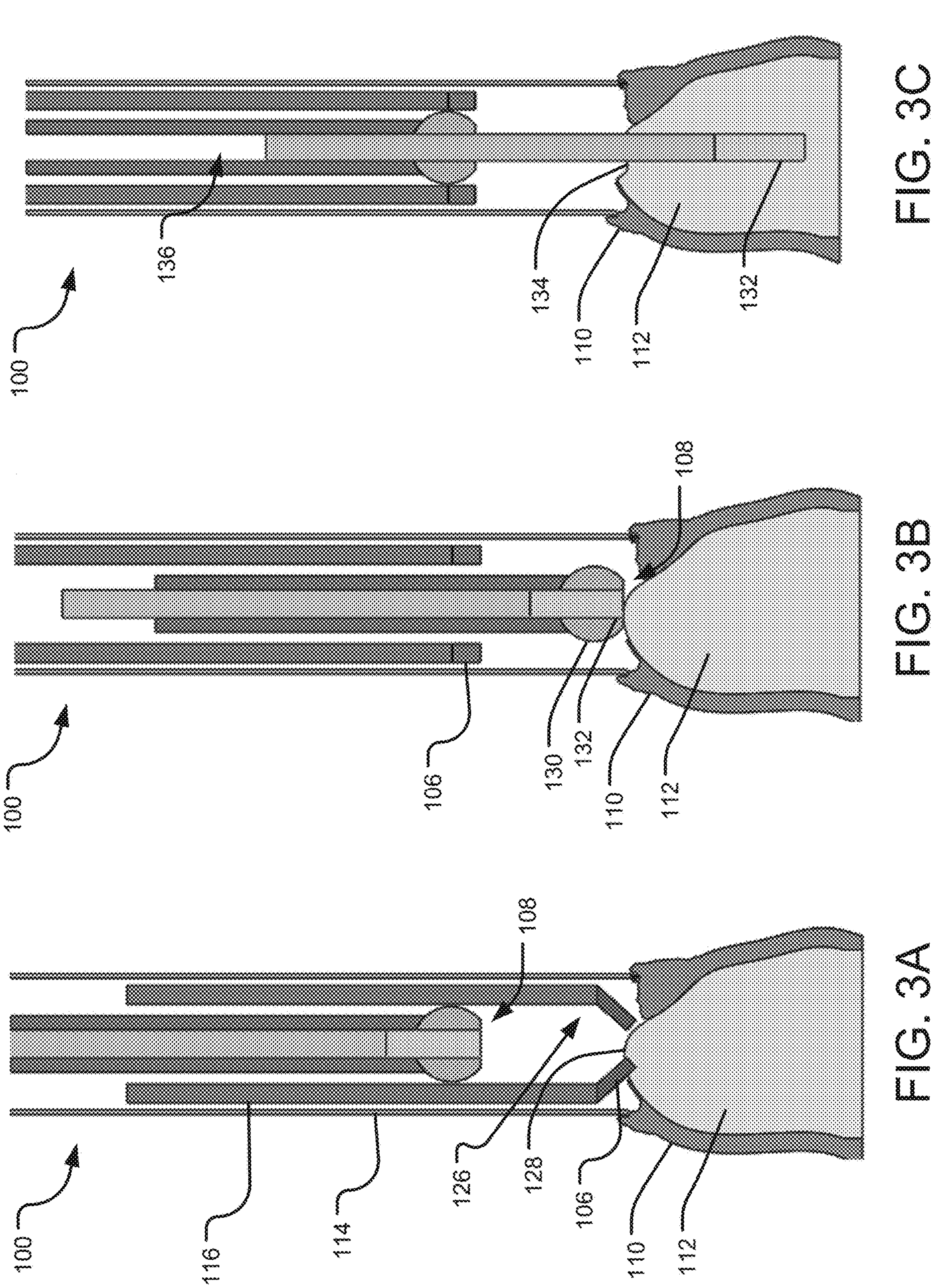
FIG. 3A depicts the drilling tool of FIG. 1 according to at least another embodiment of the present disclosure.
FIG. 3B depicts the drilling tool of FIG. 1 according to at least another embodiment of the present disclosure.
FIG. 3C depicts the drilling tool of FIG. 1 according to at least another embodiment of the present disclosure.

FIGS. 3A-3C illustrate use of the retractable brush 106 and the at least one drill 108. The brush 106 extends from an end 126 of the second casing 116. The second casing 116 (and thus, the brush 106) is retractable, extendable, and/or rotatable within the first casing 114. The brush 106 is independently extendable and retractable between a retracted position and an extended position, although in some embodiments the brush 106 may be fixed in position at the end of the second casing 116. As described above, the brush 106 (and/or the second casing 116) may move the dilator 102 from the undilated position to the dilated position when the brush 106 (and/or the second casing 116) is extended from a retracted position to an extended position. The brush 106 (and/or the second casing 116) may remain or be returned to the retracted position when the brush 106 is not in use, thus keeping the brush 106 out of the way when other components (e.g., the dilator 102, the cutter 104, and/or the at least one drill 108) are being used.

The retractable brush 106 is configured to brush the anatomical element 112 of the patient to remove matter from a surface 128 of the anatomical element 112 and thus prepare the surface 128 for cutting and/or drilling, as shown in FIG. 3A. In some examples, the brush rotates and removes tissue from a bone. The brush 106 may be cleaned after use and/or may be replaceable. The brush 106 may be formed of or otherwise comprise steel bristles, though in other examples, the brush 106 may be formed of or otherwise comprise bristles of another metal or metal alloy, plastic bristles, or any other suitable material. In some embodiments, the brush may comprise a plurality of non-aligned filaments (such as, for example, steel wool or wire sponge), or may otherwise be formed without generally aligned bristles. The brush 106 may extend around an entire perimeter of the end 126 of the second casing 116, or the brush 106 may extend partially around, or may be segmented along, the perimeter. Similarly, as shown in the illustrated example, the brush 106 may extend around or partially around the at least one drill 108.

The at least one drill 108 is disposed inside of the first casing 114 and the second casing 116 when fully retracted, and is disposed outside of the second casing 116 when extended. The at least one drill 108 may be disposed inside of the first casing 114 when partially extended and in use, as shown in FIG. 3B, or may be disposed outside of the first casing 114 when extended and in use, as shown in FIG. 3C. During use, the at least one drill 108 is configured to drill into the anatomical element 112.

In the illustrated embodiment, the at least one drill 108 comprises a first drill 130 and a second drill 132. In other embodiments, the at least one drill may comprise one drill, or more than two drills. In the illustrated embodiment, the second drill 132 is disposed in a cannula 136 of the first drill 130, though in other embodiments, the second drill 132 may be disposed adjacent to or spaced from the first drill 130. Each of the first drill 130 and the second drill 132 are removable from the tool 100 for cleaning, repairing, or replacing. Each of the first drill 130 and the second drill 132 are independently and/or together retractable or expandable. For example, the first drill 130 may be retracted and the second drill 132 may be extended, the first drill 130 may be extended and the second drill 132 may be retracted, and/or both the first drill 130 and the second drill 132 may be extended or retracted. Further, the first drill 130, the second drill 132, and the brush 106 are each independently retractable or expandable.

In the illustrated embodiment, the first drill 130 comprises a burr or rotary file configured to create a flat or dimple 134 on the surface 128 of the anatomical element 112, shown in FIG. 3B, and the second drill 132 comprises a drill bit configured to drill a hole through the flat 134, shown in FIG. 3C. In other embodiments, the first drill 130 may comprise a drill bit or any other type of rotary drilling or cutting implement and the second drill 132 may comprise a burr rotary file or any other type of rotary drilling or cutting implement. As shown in FIG. 3B, both the burr and the drill bit may extend when the burr is in use. During use, both the burr and the drill bit may rotate together, or the burr may rotate while the drill bit remains stationary. The flat 134 created by the burr provides for a clean, flat surface perpendicular to the drill bit, so as to beneficially reduce or prevent skiving of the drill bit. In other words, the flat 134 provides an angle of attack for the drill bit that will improve the drill bit's ability to engage the anatomical element 112. In some embodiments, however, the drill bit may drill the hole through the anatomical element 112 without the burr creating the flat 134.

During use of the tool 100, the brush 106 and/or the first drill 130 may be retracted when the drill bit is drilling the hole. After the drill bit drills the hole, the tool 100 may be removed from the patient. Prior to removal, any of the components (e.g., the brush 106, the first drill 130, and/or the second drill 132) may be retracted, if not already retracted, and the dilator 102 may be moved to the undilated position, though it will be understood that the dilator 102 may remain in the dilated position during removal of the tool 100. In other embodiments, one or more components of the tool 100 may remain extended during removal of the tool 100 from the patient.

Each of the various components of the tool 100 may be made of a metal, a metal alloy, a plastic, a composite, any other suitable material that enables the component to achieve the purpose thereof as described herein, and/or any combination of the foregoing. In some embodiments, one or more components of the tool 100 may be made of a radiolucent material, such as polyetheretherketone (PEEK) or thermoplastic resins with carbon-fiber reinforcement. In other embodiments, none of the components of the tool 100 are radiolucent. The material(s) from which the various components of the tool 100 are made may be selected to enable the tool 100 and/or one or more portions thereof to be cleanable, sterilizable (whether by heat, chemical treatment, or otherwise), and/or reusable. Additionally and/or alternatively, the material(s) from which the various components of the tool 100 are made may be selected for ease of cleaning, replaceability, or repair.

Figure 4:
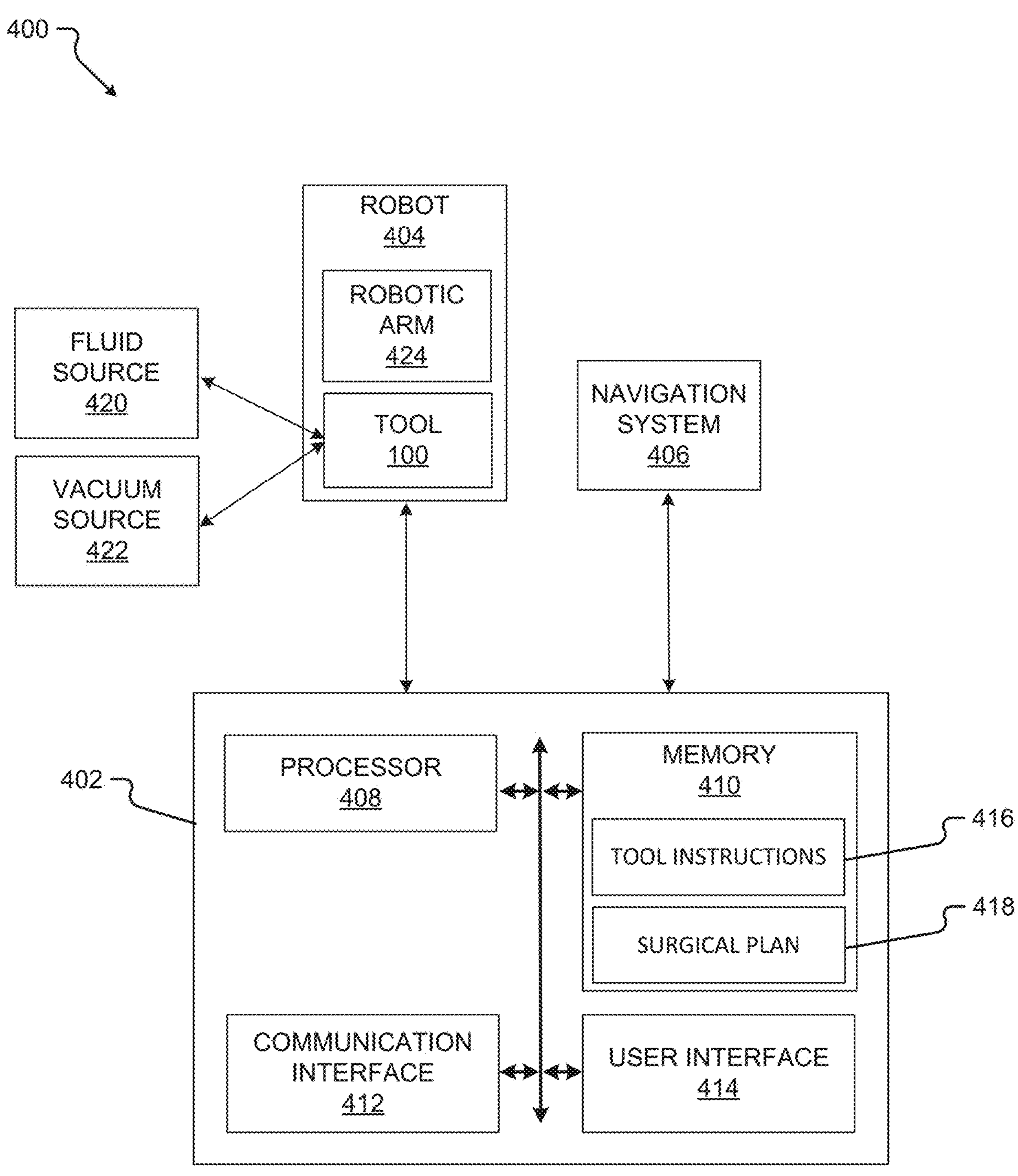
FIG. 4 is a block diagram of a system according to at least one embodiment of the present disclosure.

The tool 100, as described above with respect to FIGS. 1-3C, may be used in a system 400, as shown in FIG. 4, though it will be understood that the tool 100 may be used independently of the system 400. The system 400 includes a computing device 402, a robot 404, the tool 100, a fluid source 420, a vacuum source 422, and/or a navigation system 406. In some embodiments of the present disclosure, systems such as the system 400 of FIG. 4 may not include one or more of the illustrated components, may include other components not shown in FIG. 4, and/or may include components similar to, but not the same as, one or more components of the system 400 shown in FIG. 4. For example, in some embodiments, the system 400 may not include the navigation system 406. In other embodiments, the system 400 may not include the fluid source 420 and/or the vacuum source 422.

The computing device 402 according to embodiments of the present disclosure may comprise a processor 408, a memory 410, a communication interface 412, and the user interface 414. A computing device such as computing device 402 in some embodiments may have more components or fewer components than the computing device 402 shown in FIG. 4.

The processor 408 of the computing device 402 may be any processor described herein or any similar processor. The processor 408 may be configured to execute instructions stored in the memory 410, which instructions may cause the processor 408 to carry out one or more computing steps utilizing or based on data received from the user interface 414; one or more sensors included in, attached to, or otherwise monitoring operation of the tool 100; the robot 404, and/or the navigation system 406.

The memory 410 may be or comprise RAM, DRAM, SDRAM, other solid-state memory, any memory described herein, or any other tangible, non-transitory memory for storing computer-readable data and/or instructions. The memory 410 may store information or data useful for completing any step of the method 500 described herein. The memory 410 may store, for example, one or more tool instructions 416 and/or one or more surgical plans 418. Such instructions 416 may, in some embodiments, be organized into one or more applications, modules, packages, layers, or engines. The instructions 416 may cause the processor 408 to manipulate data stored in the memory 410 and/or received from the navigation system 406.

The computing device 402 may also comprise a communication interface 412. The communication interface 412 may be used for receiving information from an external source (such as the tool 100, the robot 404, and/or the navigation system 406), and/or for transmitting instructions, data, or other information to an external system or device (e.g., the tool 100, the robot 404, and/or the navigation system 406). The communication interface 412 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 412 may be useful for enabling the computing device 402 to communicate with one or more other processors 408 or computing devices 402, whether to reduce the time needed to accomplish a computing-intensive task or for any other reason.

The computing device 402 may also comprise one or more user interfaces 414. The user interface 414 may be or comprise a keyboard, mouse, trackball, monitor, television, touchscreen, joystick, switch, button, and/or any other device for receiving information from a user and/or for providing information to a user. The user interface 414 may be used, for example, to receive a user selection or other user input regarding a surgical plan; to receive user input useful in connection with the tool instructions 416 and/or the surgical plan 418, to receive a user selection or other user input regarding operation of the robot 404, manipulation of the robotic arm 424, and/or use of the tool 100; and/or to display the instructions 416 and/or the surgical plan 418. In some embodiments, the user interface 414 may be useful to allow a surgeon or other user to modify the instructions 416, the plan 418, or other information displayed, though it will be appreciated that each of the preceding inputs may be generated automatically by the system 400 (e.g., by the processor 408 or another component of the system 400) or received by the system 400 from a source external to the system 400. In some embodiments, user input such as that described above may be optional or not needed for operation of the systems, devices, and methods described herein.

Although the user interface 414 is shown as part of the computing device 402, in some embodiments, the computing device 402 may utilize a user interface 414 that is housed separately from one or more remaining components of the computing device 402. In some embodiments, the user interface 414 may be located proximate one or more other components of the computing device 402, while in other embodiments, the user interface 414 may be located remotely from one or more other components of the computing device 402.

The robot 404 may be any surgical robot or surgical robotic system. The robot 404 may be or comprise, for example, the Mazor X™ Stealth Edition robotic guidance system. The robot 404 may comprise one or more robotic arms 424. In some embodiments, the robotic arm 424 may comprise one robotic arm, though in other embodiments, the robotic arm 424 may comprise two robotic arms or more than two robotic arms. The tool 100 may be disposed on an end of the robotic arm 424. In other examples, the tool 100 may be disposed on any portion of the robotic arm 424 and/or the robot 404.

Reference markers (i.e., navigation markers) may be placed on the robot 404, the robotic arm 424, the tool 100, or any other object in the surgical space. The reference markers may be tracked by the navigation system 406, and the results of the tracking may be used by the robot 404 and/or by an operator of the system 400 or any component thereof. In some embodiments, the navigation system 406 can be used to track other components of the system (e.g., the tool 100) and the system 400 can operate without the use of the robot 404 (e.g., with the surgeon manually manipulating the tool 100).

In some embodiments, the system 400 may include a navigation system 406, though in other embodiments, the system 400 may not include a navigation system 406. The navigation system 406 may provide navigation for a surgeon and/or a surgical robot during an operation. The navigation system 406 may be any now-known or future-developed navigation system, including, for example, the Medtronic StealthStation™ S8 surgical navigation system. In various embodiments, the navigation system 406 may be used to track a position of the robotic arm 424 (or, more particularly, of a navigated tracker attached to the robotic arm 424). The navigation system 406 may include a camera or other sensor(s) for tracking one or more reference markers, navigated trackers, or other objects within the operating room. The navigation system 406 may include a display for displaying one or more images from an external source (e.g., the computing device 402, camera, or other source) or a video stream from the camera or other sensor of the navigation system 406. In some embodiments, the navigation system 406 may provide position, movement, and/or other information to the computing device 402 for use in controlling the tool 100 and/or any other aspect of the system 400. In some embodiments, the system 400 can operate without the use of the navigation system 406.

The system 400 may also include a fluid source 420 and/or a vacuum source 422. In some embodiments, the system 400 does not include the fluid source 420 and/or the vacuum source 422, may include only the fluid source 420, or may include only the vacuum source 422. In other embodiments, the fluid source 420 and/or the vacuum source 422 may be used with the tool 100 independently of the system 400. Each of the fluid source 420 and/or the vacuum source 422 may be formed as a part of the tool 100 or may be separate from the tool 100. A hose (not shown) may extend from each of the fluid source 420 and the vacuum source 422 to the tool 100. The fluid source 420 may be configured to provide fluid to the brush 106 and/or the at least one retractable drill 108. The fluid may be a gas (e.g., oxygen, air, carbon dioxide, heliox) or a liquid (water, saline, etc.). The fluid may cool the drill 108 during use and/or flush loose anatomical particles from the drill 108, the brush 106, and/or anatomical element 112. The vacuum source 422 may remove the fluid when used with the fluid source 420 and/or may remove loose anatomical particles when used with or without the fluid source 420. The fluid may be delivered to the anatomical element 112 and/or removed from the anatomical element by a cannula in the at least one drill 108. In other embodiments, the fluid may be delivered to or removed from the anatomical element 112 through any cannula, annulus, or hose formed on, disposed on, or connected to the tool 100.

Figure 5:
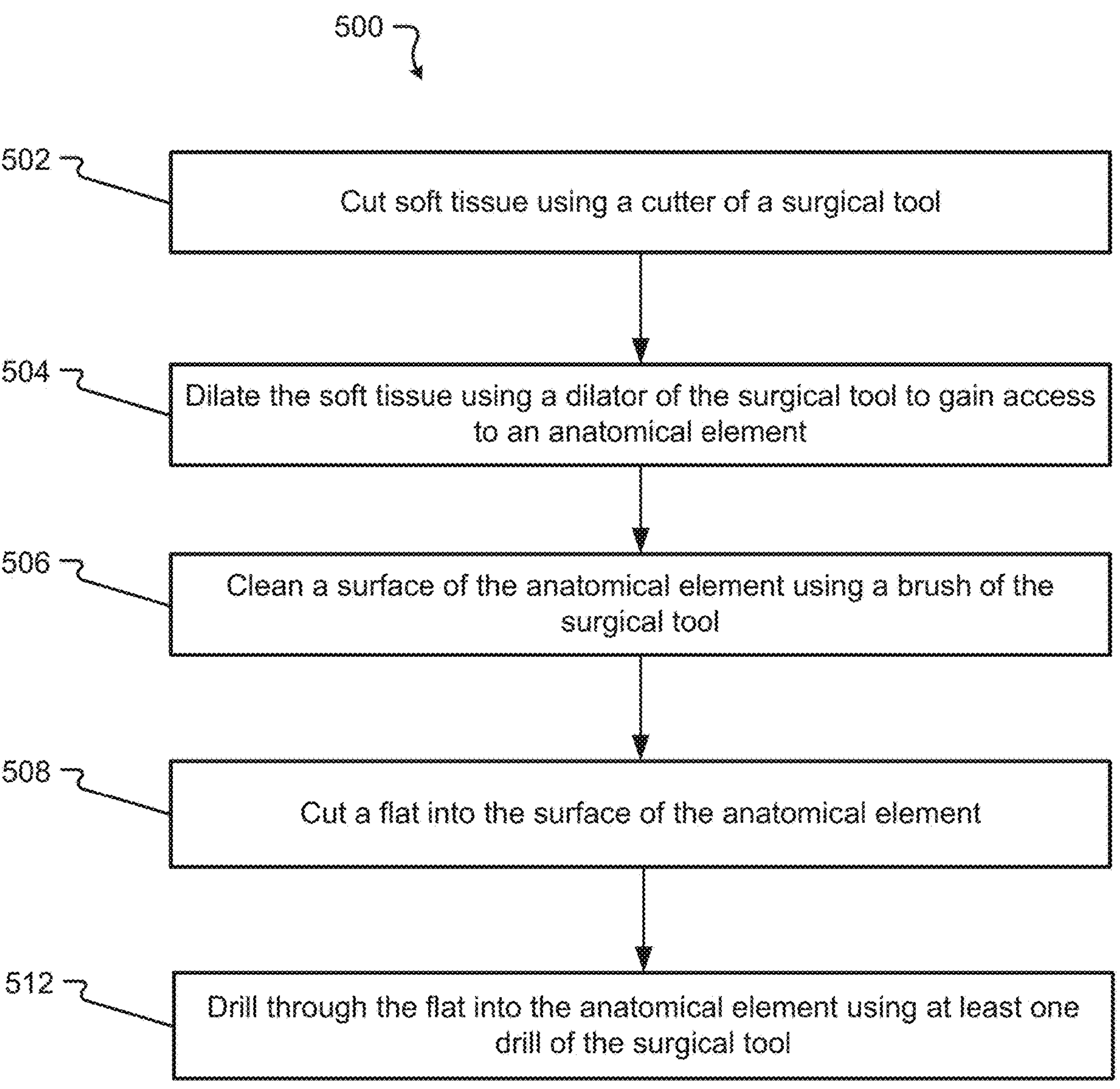
FIG. 5 is a flowchart of a method according to at least one embodiment of the present disclosure.

Turning now to FIG. 5, a method 500 for performing a surgical procedure may be executed in whole or in part by a robot (e.g., a robot 404 controlled by a computing device 402) and/or a surgeon. The method 500 may be performed using, for example, the tool 100 described above with respect to FIGS. 1-3 and/or the system 400 described above with respect to FIG. 4.

The method 500 comprises causing a cutter (e.g., the cutter 104) of a surgical tool (e.g., the surgical tool 100) to cut the soft tissue (e.g., the tissue 110) of a patient (step 502). As described with respect to FIGS. 1A-2B, the cutter may create an incision in the soft tissue to form an opening (such as, for example, the opening 124) and thus provide access to an anatomical element such as the anatomical element 112.

The method 500 also comprises causing a dilator (e.g., the dilator 102) of the tool to dilate the soft tissue (step 504). As previously described with respect to FIGS. 2A-2B, the dilator dilates the opening to form a larger opening through which further components of the tool may be inserted. During the dilation step, in which the dilator moves from the undilated position to the dilated position, the cutter may simultaneously move from the cutting position to the non-cutting position, shown in FIG. 2B.

The method 500 further comprises causing a brush (e.g., the brush 106) of the tool to brush a surface (e.g., the surface 128) of the anatomical element (step 506). As previously described with respect to FIG. 3A, the brush brushes and/or cleans the surface by removing any remaining soft tissue from the surface of the anatomical element to prepare the surface for drilling (e.g., by the first drill 130 or burr).

The method 500 also comprises cutting a flat or dimple into the surface of the anatomical element (step 508). The cutting the flat or dimple may be accomplished using a burr or rotary file such as the first drill 130. The flat or dimple may act as a guide for a drill bit used to drill into the anatomical element, and/or may beneficially help to prevent skiving during drilling. The flat or dimple may have a circular shape, and may have a diameter at least as large as a diameter of a drill bit used to drill into the anatomical element.

The method 500 also comprises causing at least one drill (which may be the same as or similar to the second drill 132 or a component thereof) to drill into the anatomical element (step 512). As previously described with respect to FIGS. 3B and 3C, the at least one drill may be, for example, the second drill 132, and may comprise a drill bit configured for drilling into bone or other hard tissue. The at least one drill may commence drilling from the flat or dimple on the surface of the anatomical element that results from the step 508.

In some embodiments, the method 500 may comprise receiving a surgical plan, which may be the same as or similar to the surgical plan 418. The surgical plan may be received via a user interface and/or communication interface of a computing device such as the computing device 402, and may be stored in a memory such as the memory 410 of the computing device 402. The surgical plan may include information about one or more planned movements of the tool during a surgical procedure. The information may also include a timeline or schedule of the one or more planned movements. The one or more planned movements may include one or more of timestamps, a type of movement (e.g., translational and/or rotational), a duration of the movement, and/or positional information (e.g., coordinates).

In some embodiments, the method 500 may comprise determining information about one or more needed movements of the tool during a surgical procedure outlined or otherwise described in a surgical plan. In such embodiments, the surgical plan may not include receiving any such information via a computing device (e.g., the computing device 402), but a processor (e.g., the processor 408), executing instructions stored in a memory (e.g., the memory 410), may generate such information based on the surgical plan.

In some embodiments, the method 500 may comprise generating tool instructions such as the tool instructions 416 for causing a tool (e.g., the tool 100) to perform one or more surgical steps such as those described in connection with the steps 502 to 512. The instructions may be based on the surgical plan. In some embodiments, however, the tool may be automatically actuated based on instructions stored in a memory thereof that are not based on a surgical plan.

The instructions 416 may include one or more instructions that cause an alert or other indication to be given to the surgeon (e.g., via a user interface such as the user interface 414) prior to each movement of the tool, and/or prior to executing one of the one or more planned surgical steps. In some embodiments, such an alert may pause execution of the surgical plan for approval by the surgeon or other operator. In other embodiments, the alert may simply notify the surgeon of the planned movement and/or of the planned volume increase or decrease, and automatically execute the planned movement. The alert and/or notification may be displayed on the user interface and/or may include a sound and/or a visual display.

In some embodiments, the method 500 may comprise positioning the tool using a robotic arm. The method 500 may also be performed automatically by the robotic arm (e.g., which may be, for example, a robotic arm 424) holding the tool. In other embodiments, the tool may be used manually by a surgeon, which surgeon may in some embodiments be assisted by a robot (e.g., the robot 404) and/or a navigation system (e.g., the navigation system 406).

As may be appreciated based on the foregoing disclosure, the present disclosure encompasses methods with fewer than all of the steps identified in FIG. 5 (and the corresponding description of method 500), as well as methods that include additional steps beyond those identified in FIG. 5 (and the corresponding description of method 500).

The methods and systems described herein provide a tool that can perform an incision and dilate the incision to gain access to an anatomical element, prepare the anatomical element for drilling, and drill the anatomical element using a single multi-function tool. The tool advantageously reduces at least four components into a single device, thereby eliminating the need for a surgeon or surgical robot to switch tools mid-procedure and resulting in reduced operating time. Further, a lack of switching tools reduces potential risk of accidental impact from a tool being removed or inserted into the surgical site. The tool can also perform each surgical step automatically and is easily removable from the surgical site as one unit. Further, the tool is held in the same position or a similar position during use, thereby ensuring that the drill bit is adequately positioned on the prepared surface.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for drilling into an anatomical element comprising:

cutting tissue of a patient using a cutter of a surgical tool;

dilating the tissue of the patient using a dilator of the surgical tool, the dilator having a plurality of arms, each arm having a free end, the plurality of arms moveable between an undilated position, in which the free ends are closer to each other to define a wedge-like configuration, and a dilated position in which the free ends are further from each other than in the undilated position, wherein the cutter of the surgical tool is attached to a free end of one arm of the plurality of arms of the dilator;

cleaning a surface of an anatomical element of the patient to remove matter from the surface using a brush of the surgical tool; and drilling into the anatomical element with at least one drill of the surgical tool.

2. The method of claim 1, wherein the method is performed automatically by a robotic arm holding the surgical tool.

3. The method of claim 1, further comprising cutting a flat into the surface of the anatomical element using the at least one drill.

4. The method of claim 1, wherein dilating the tissue includes extending the brush adjacent the dilator to move the plurality of arms from the undilated position to the dilated position.

5. The method of claim 1, further comprising automatically retracting the brush when the at least one drill is extended.

6. The method of claim 5, wherein the dilator locks into the dilated position when the brush is automatically retracted.

7. The method of claim 1, wherein cleaning the surface of the anatomical element of the patient with the brush of the surgical tool comprises rotating the brush of the surgical tool.

8. The method of claim 1, further comprising automatically moving the cutter between a cutting position and a non-cutting position based on the dilator being in the dilated or undilated position.

9. The method of claim 1, wherein the at least one drill comprises a first drill and a second drill, the second drill used after the first drill to drill into the anatomical element.

10. The method of claim 9, wherein the second drill is disposed in a cannula of the first drill.

* * * * *